United States Patent [19]

Nakamura et al.

[11] Patent Number: 4,801,204
[45] Date of Patent: Jan. 31, 1989

[54] METHOD AND APPARATUS FOR MEASURING THE TURBIDITY OF LIQUID MEDIA

[75] Inventors: Takashi Nakamura, Kawasaki; Motohiko Hikuma, Yokohama; Takahiro Kuratani, Kawasaki; Haruo Obana, Tokyo; Yasutsugu Morita, Tokyo, all of Japan

[73] Assignee: Ajinomoto Co., Inc., Tokyo, Japan

[21] Appl. No.: 754,212

[22] Filed: Jul. 12, 1985

[30] Foreign Application Priority Data

Jul. 12, 1984 [JP] Japan .................. 59-145192

[51] Int. Cl.⁴ .................. G01N 21/26; C12K 1/04
[52] U.S. Cl. .................. 356/338; 250/574
[58] Field of Search .............. 356/336, 342, 442, 338, 356/441, 343, 339; 250/574

[56] References Cited

U.S. PATENT DOCUMENTS

| | | | |
|---|---|---|---|
| 2,892,378 | 6/1959 | Canada | 250/574 |
| 3,665,201 | 5/1972 | Shea et al. | 356/342 |
| 3,714,444 | 1/1973 | Carr et al. | 356/442 |
| 3,819,278 | 6/1974 | Muller | 356/442 |
| 4,021,120 | 5/1977 | Muller et al. | 356/442 |
| 4,075,062 | 2/1978 | Shibata et al. | 356/442 |
| 4,146,799 | 3/1979 | Pitt et al. | 356/343 |
| 4,155,652 | 5/1979 | Buchan et al. | 356/342 |
| 4,201,477 | 5/1980 | Palmer et al. | 356/442 |
| 4,283,143 | 8/1981 | Patterson | 356/339 |

FOREIGN PATENT DOCUMENTS 1959612  6/1971  Fed. Rep. of Germany ...... 356/432

*Primary Examiner*—R. A. Rosenberg
*Attorney, Agent, or Firm*—Oblon, Fisher, Spivak, McClelland & Maier

[57] ABSTRACT

The method of the present invention which relates to the measurement of the turbidity of a liquid media, is characterized by the following steps.
(i) Placing a measuring cell having a sensor having a light-receiving surface in contact with the liquid media, wherein the light-receiving surface is oriented in a direction permitting bubbles dissolved in the liquid media to float away therefrom and out of the cell.
(ii) Cleaning the light-receiving surface intermittently.
(iii) Allowing bubbles in the cell to float out of the cell.
(iv) Radiating light in the liquid media.
(v) Detecting scattered light impinging on the light-receiving surface.

The present invention also provides an apparatus for measurement of liquid media turbidity in accordance with the present invention.

14 Claims, 3 Drawing Sheets

METHOD AND APPARATUS FOR MEASURING THE TURBIDITY OF LIQUID MEDIA

BACKGROUND OF THE INVENTION

1. Field of the Invention

The present invention relates to a method for measuring the turbidity of a liquid media. More particularly, it relates to a turbidimetric method and apparatus which are suitable for determining the concentration of a suspended substance in activated sludge or pulp waste, or the concentration of microorganisms in a fermented solution or waste of fermentation.

2. Discussion of the Background

Various methods exist for measuring the turbidity (concentration) of a liquid media. These methods are based on ultrasounds, radioactive materials, or light. Methods based on light are classified into (1) methods which use transmitted light or (2) methods which use scattered light. With either of the light-based methods, the presence of bubbles in the liquid media greatly limits measurement accuracy. As a matter of fact, no method currently exists for the on-line determination of the concentration of microorganisms in a fermentation process.

A variety of methods have been proposed for removing bubbles. Some of these are:

(1) Adding an antifoaming agent to the liquid to be analyzed;

(2) Applying pressure to the liquid in a sampler;

(3) Using a bubble removal net;

(4) Using a sampler having an inner tube and an outer tube and causing a liquid to flow up the inner tube and down the outer tube so that bubbles rising in the outer tube may be separated from the liquid; or (5) Drawing a liquid into a sampler by a piston and leaving the liquid at rest so that bubbles rising in the sampler may be discharged through its liquid inlet.

The conventional methods as hereinabove described, however, suffer from the following problems.

(a) All of these methods suffer from measurement inaccuracy due to the presence of bubbles;

(b) The optical systems used are easily contaminated, resulting in measurement inaccuracy; and (c) Turbidimeters are complicated in construction and easily stained, resulting in contamination by varied germs, especially in fermentations and other cultivations media.

Thus, there is a strongly felt need for a method for accurately measuring the turbidity of liquid media and/or fermentation media, wherein the method does not suffer from the drawbacks outlined above: measurement inaccuracy due to the presence of bubbles in the media or optical system contamination; or media contamination due to turbidimeter design. Likewise, there is a strong need for a method and apparatus for efficiently, quickly and accurately measuring liquid media.

SUMMARY OF THE INVENTION

Accordingly, one object of the present invention is to provide a method for efficiently measuring the turbidity of liquid media.

It is another object of the present invention to provide a method for measuring the turbidity of liquid media, where the measurement is characterized by a quick response time.

It is another object of the present invention to provide a method for accurately measuring the turbidity of liquid media.

It is another object of the present invention to provide a method for measuring the turbidity of liquid media, where the method does not suffer from bubble related measurement inaccuracy.

It is another object of the present invention to provide a method for measuring the turbidity of liquid media, where the method does not suffer from optical system contamination related measurement inaccuracy.

It is another object of the present invention to provide a method for measuring the turbidity of liquid media, where the method does not result in media contamination.

It is another object of the present invention to provide an apparatus which satisfies each and everyone of the above objects of the present invention.

The method of the present invention is characterized by the following steps.

(i) Placing a measuring cell having a sensor having a light-receiving surface in contact with the liquid media, wherein the light-receiving surface is oriented in a direction permitting bubbles dissolved in the liquid media to float away therefrom and out of the cell.

(ii) Cleaning the light-receiving surface intermittently.

(iii) Allowing bubbles in the cell to float out of the said cell.

(iv) Radiating light in the liquid media.

(v) Detecting scattered light impinging on the light-receiving surface.

According to another feature of the method of the invention, the method comprises the steps of isolating a portion of the liquid media, permitting bubbles in the isolated portion of the liquid media to float away from the isolated portion while preventing bubbles from a remainder of the liquid media from entering the isolated portion, radiating light into the isolated portion of the liquid media and detecting radiated light scattered from the isolated portion of the liquid media. The steps of isolating a portion of the liquid media and permitting bubbles in the isolated portion of the liquid media to float away from the isolated portion while preventing bubbles from a remainder of the liquid media from entering the isolated portion is accomplished by placing in the liquid media a cylindrical body having an upwardly directed open end, the cylindrical body being otherwise closed. The bubbles from the isolated portion can float out of the open end but bubbles from the remainder of the liquid media cannot enter the isolated portion via the open end. The cylindrical body has a light receiving surface which can be cleaned by intermittently blowing air therepast.

The present invention also provides an improved measuring cell. This cell is characterized by a simplified construction which facilitates the removal of bubbles and the cleaning of a light receiving surface. This cell may be used in conjunction with an optical fiber system for detecting scattering light.

The apparatus of the present invention is characterized by having a light sensor containing at least one optical fiber in a cylindrical body. This cylindrical body has a light-receiving surface and a measuring cell for holding the liquid media to be analyzed. The cell has one end joined to the sensor, another end which is open, and a means for intermittently cleaning the light-receiving surface.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein:

In FIGS. 4 and 6, a indicates the output voltage recorded when the light receiving surface was wiped by hand and b indicates the output voltage recorded thereafter.

DETAILED DESCRIPTION OF THE PREFERRED EMBODIMENTS

Figure 1:
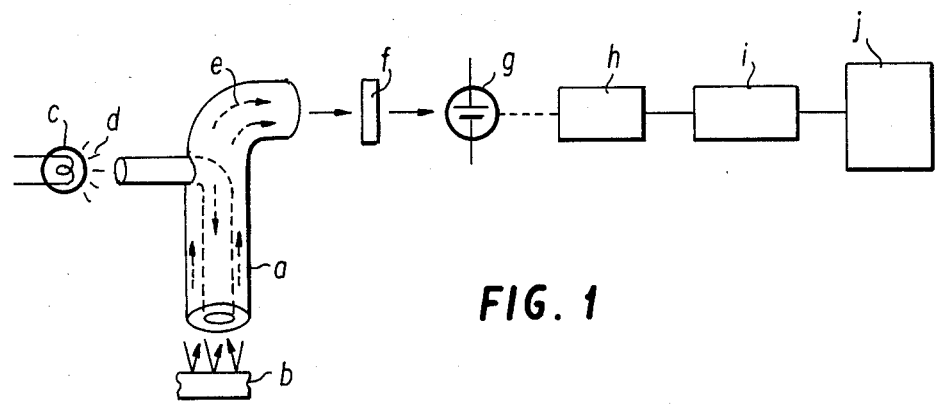
FIG. 1 is a block diagram of a measuring system showing the principle of this invention.

The method of this invention comprises isolating a measuring cell in the liquid media to be analyzed in such a way that a sensor may have a light receiving surface looking upward relative to a horizontal plane, supplying air intermittently to clean the light receiving surface, allowing bubbles to float to the surface to remove them from the cell, preventing other bubbles from entering the cell radiating light into the liquid and detecting scattered light via the sensor.

The apparatus of the present invention is made up of a sensor containing at least one optical fiber in a cylindrical body having at one end a light receiving surface and a measuring cell for holding the liquid to be analyzed. The cell has one end joined to one end of the sensor body and another end that is open, the cell has a cylindrical wall formed at the one end of the cell with a gas, e.g., air nozzle substantially facing the light receiving surface, and means for supplying air under pressure to the nozzle intermittently.

The method of the present invention is characterized by the following steps.

(i) Placing a measuring cell having a sensor having a light-receiving surface in contact with the liquid media, wherein the light-receiving surface is oriented in a direction permitting bubbles dissolved in the liquid media to float away therefrom and out of the cell but bubbles from the remainder of the liquid media are prevented from entering the measuring cell.

(ii) Cleaning the light-receiving surface intermittently.

(iii) Allowing bubbles in the cell to float out of the said cell.

(iv) Radiating light in the liquid media.

(v) Detecting scattered light impinging on the light-receiving surface.

In a preferred embodiment the light-receiving surface is oriented in an orientation skewed from a vertical plane.

In another preferred embodiment the light-receiving surface is cleaned by the action of a gas supplied intermittently thereto.

In another preferred embodiment the gas comprises gases which are well known in this art, such as, for example, nitrogen, air, etc.

The apparatus of the present invention is characterized by having a light sensor containing at least one optical fiber in a cylindrical body. This cylindrical body has a light-receiving surface and a measuring cell for holding the liquid media to be analyzed. The cell has one end joined to the sensor, another end which is open, and a means for intermittently cleaning the light-receiving surface.

In a preferred embodiment, the means for cleaning the light-receiving surface comprises a gas nozzle substantially facing the light-receiving surface.

In another preferred embodiment, the apparatus comprises a means for supplying, intermittently, gas under pressure to the nozzle.

In another preferred embodiment, the gas used may be any gas well known in this art, such as, for example, nitrogen, air, etc.

The invention as hereinabove described has the following advantages:

(1) The apparatus is so simple in construction that it is easy to manufacture, operate and inspect;

(2) Bubbles are easy to remove and do not have any adverse effect on measurement;

(3) The supply of gas, e.g., air, through the nozzle protects the optical system (light receiving surface) against contamination;

(4) It is sufficient to immerse the apparatus in the liquid to be analyzed in order to achieve the online measurement of its turbidity easily; and (5) Good efficiency and reproducibility, and accurate measurement are readily obtained.

Referring now to the drawings, wherein like reference numerals designate identical or corresponding parts throughout the several views, and more particularly to FIG. 1 thereof, light d is radiated from a light source c to a fluid b flowing about optical fiber a, and scattered by a suspended substance in the fluid b. The backwardly scattered light e passes through the optical fiber and is filtered by an interference filter f (e.g. 560 nm). It is converted by a photodiode g to an output voltage. The output voltage is transmitted through an amplifier h and a filter i and recorded on a recorder j. The voltage is read from the recorder and used for calculating the turbidity of the liquid media.

Figure 2:
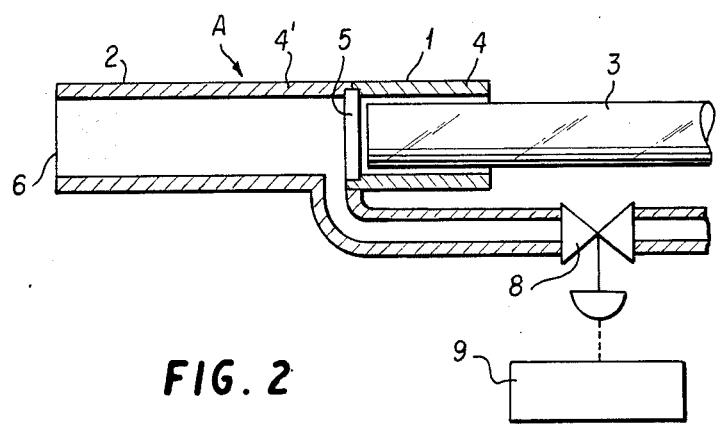
FIG. 2 is a longitudinal sectional view of an apparatus embodying this invention.

FIG. 2 shows a turbidity measuring apparatus (turbidimeter) embodying the present invention. The turbidimeter A comprises optical fiber 3, a protective cover 1 for the optical fiber and a measuring cell 2 for holding the liquid media to be analyzed. The cover 1 comprises a cylindrical body 4 for protecting the optical fiber 3 and a transparent glass light receiving surface 5 or light-transmitting plastic light receiving surface 5 (serving also as a light projecting surface) provided at one end of the body 4. The measuring cell 2 comprises a cylindrical body 4' extending from the light receiving surface 5 and terminating in an open end 6. The body 4' is formed at one end with a gas (e.g., air) nozzle 7 substantially facing the light receiving surface 5. The nozzle 7 is provided with an electromagnetic valve 8 which is alternately turned on and off at regular intervals for supplying gas (e.g., air) under pressure to the light receiving surface 5 intermittently. A timer 9 is provided for the valve 8.

A method for the on-line measurement of the turbidity of a liquid media will now be described.

The apparatus of this invention is immersed in the liquid media to be analyzed on line, and so positioned that the light receiving surface 5 may be oriented in a direction skewed from a vertical plane. If the liquid media to be analyzed flows through a pipe, the cell 2 is so positioned that its open end 6 may be oriented upward from a horizontal plane.

The electromagnetic valve 8 is alternately turned on and off at regular intervals to blow air against the light receiving surface 5 intermittently through the nozzle 7. This air removes all staining matter from the light receiving surface 5 and keeps the same clean. The air also serves to prevent any old liquid media from remaining in the cell 2 and enables fresh liquid media to fill the cell 2. When the air supply is discontinued, bubbles rise along the cell 2 and are separated from the liquid media. However bubbles from outside the measuring cell are prevented from entering therein, due to the orientation of the cell. When all bubbles have been separated from the liquid media, it is possible to measure its turbidity.

The measuring system (FIG. 1) is connected to the optical fiber 3. The light scattered by the liquid media is converted to an electric current by the photodiode g. Its output voltage is read and compared with a working (calibration) curve, which has been prepared beforehand, whereby it is possible to determine the turbidity or concentration of the liquid media. Upon completion of the measurement, the electromagnetic valve 8 is turned on and off to blow air into the cell 2 to clean the light receiving surface 5 and purge the cell 2 so that the apparatus may be ready for another cycle of measurement.

Although the duration of air supply through the nozzle 7 depends on the nature of the liquid media to be analyzed, a period of two to 10 seconds is usually sufficient for satisfactory cleaning and purging purposes. While the time required for the removal of bubbles also depends on the nature of the liquid, it has been found that a period of several tens of seconds (e.g. 20 seconds to $10^4$ seconds) is sufficient for the complete defoaming of activated sludge, and a period of one to two minutes for a fermented amino acid solution.

Other features of the invention will become apparent in the course of the following descriptions of exemplary embodiments which are given for illustration of the invention and are not intended to be limiting thereof.

EXAMPLE 1

A small fermentation vessel having a capacity of one liter was charged with 600 ml of cane molasses and a turbidimeter according to this invention was inserted therein so that it might look upward at an angle of 70° to a vertical plane (i.e., 20° to a horizontal plane). *Brevibacterium lactofermentum* (ATCC 13869) was cultured in the vessel at an aeration rate of 600 ml/min. and an agitating speed of 1000 rpm. The turbidimeter's performance in complete defoaming was examined as follows.

Figure 3:
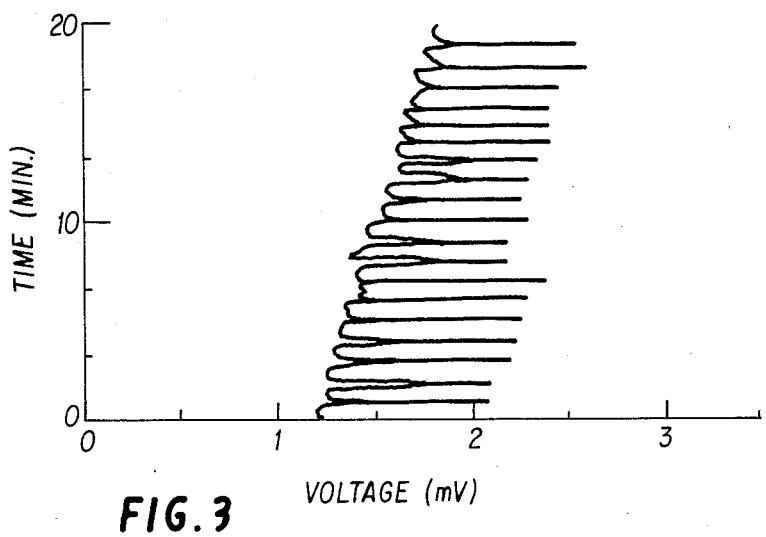
FIG. 3 is a graph showing the relation between time and output voltage according to the results of a test conducted in accordance with this invention to see if a liquid to be analyzed (*Brevibacterium lactofermentum*) was defoamed.

Air was supplied through the nozzle at a rate of 600 ml/min. intermittently for a period of 30 seconds followed by an interruption of 2.5 minutes. The intermittent supply of air was continued throughout the period of the culture. When the supply of air was interrupted, bubbles were separated from the liquid and the output voltage of the system dropped to a substantially constant level, as shown in FIG. 3. As the culture proceeded, the value of the said constant level output voltage showed an increase indicating the growth of microorganisms.

EXAMPLE 2

Figure 4:
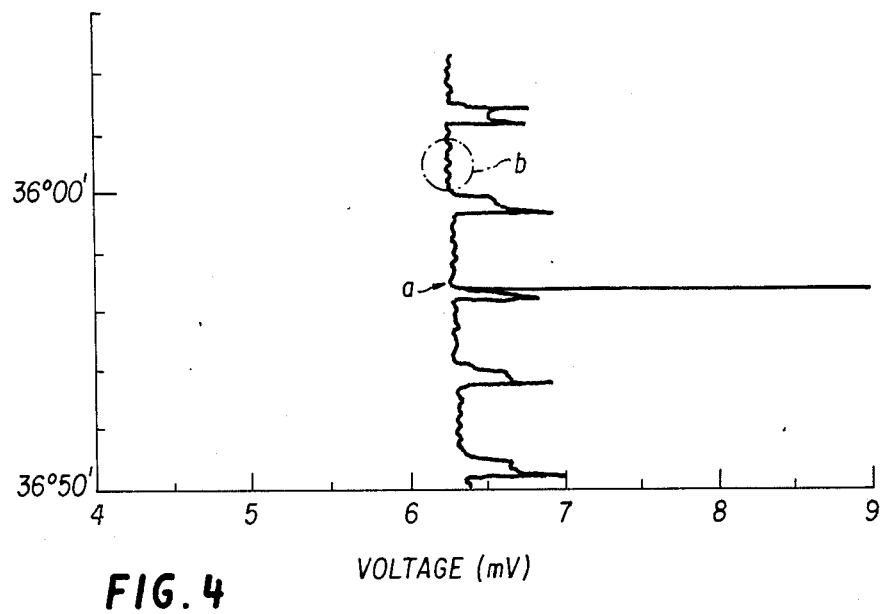
FIG. 4 is a graph showing the relation between time and output voltage according to the results of a test conducted in accordance with this invention to see if the light receiving surface was contaminated by the liquid to be anlyzed (cane molasses).

The test of EXAMPLE 1 was continued until after the cane molasses had been consumed by the microorganisms resulting in the termination of their growth. When 36 hours had passed after the beginning of the culture, the light receiving surface (protective glass) of the turbidimeter was wiped carefully by hand. Comparison was made between the output voltage in an area marked b in FIG. 4 before and after the wiping. No difference deviating from a tolerable range was found, as is obvious from FIG. 4.

EXAMPLE 3

Figure 5:
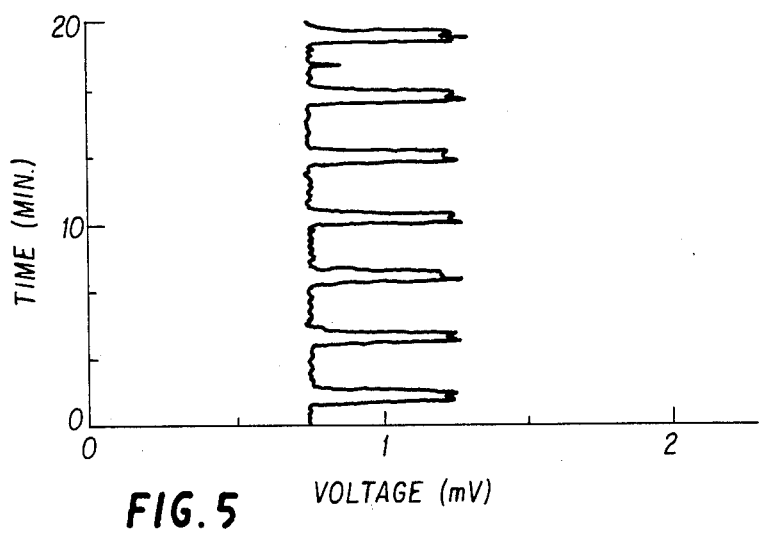
FIG. 5 is a graph showing the relation between time and output voltage as found when the supply of air was interrupted.

A vessel having a capacity of one liter was charged with 600 ml of water and 2.2 g per liter of activated sludge which had been collected from processed sewage. A turbidimeter according to this invention was inserted therein so that it might look upward at an angle of 20° of the horizontal. The contents of the vessel were aerated at a rate of 600 ml/min. and agitated at a speed of 1100 rpm. The procedure of EXAMPLE 1 was repeated for the intermittent supply of air through the nozzle. When the supply of air was interrupted, bubbles were separated from the liquid and the output voltage dropped to a substantially constant level, as shown in FIG. 5.

EXAMPLE 4

Figure 6:
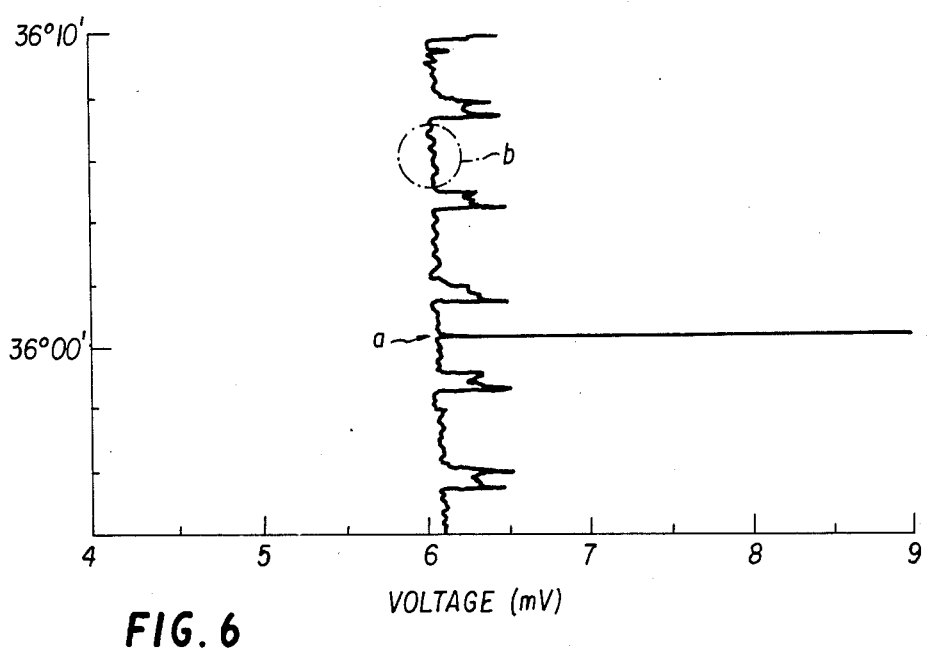
FIG. 6 is a graph showing the relation between time and output voltage according to the results of a test conducted in accordance with the present invention to see if the light receiving surface was contaminated in the test situation of FIG. 5.

The test of EXAMPLE 3 was continued for 100 hours and the light receiving surface was examined as to whether it had been contaminated. When the 100 hours had passed, the light receiving surface was wiped carefully by hand, and comparison was made between the output voltages in the area marked b in FIG. 6 before and after the wiping. No difference deviating from a tolerable range was found, as is obvious from FIG. 6.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for on-line measurement of the turbidity of a liquid media, said method comprising:
   (i) placing an apparatus for measuring the turbidity of a liquid media in a liquid media, said apparatus comprising a cylindrical body, a light sensor including at least one optical fiber in said cylindrical body, said cylindrical body having a light-receiving surface and a measuring cell adjacent said light receiving surface for holding the said liquid media to be analyzed, wherein said light sensor comprises means for radiating light through said light-receiving surface and into said measuring cell, and further comprises means for detecting scattered light impinging on said light-receiving surface, said cell having one end joined to said sensor, another end which is open, and a means for intermittently cleaning the said light-receiving surface, wherein said apparatus is oriented in a direction permitting bubbles dissolved in the said liquid media within said measuring cell to float away therefrom and out of the cell through said open end and preventing bubbles outside of said cylindrical body from entering said cell;

(ii) introducing a portion of said liquid media into said measuring cell;

(iii) allowing bubbles in the said measuring cell to float out of the said cell;

(iv) radiating light in the said liquid media via the said optical fiber; and (v) detecting scattered light impinging on the said light-receiving surface.

2. The method of claim 1 wherein the said light receiving surface is oriented in an orientation skewed from a vertical plane.

3. The method of claim 1 wherein the said light receiving surface is cleaned by the action of a gas supplied intermittently thereto.

4. The method of claim 3, wherein the said gas comprises air.

5. The method of claim 1, wherein the said measuring cell is placed into the said liquid media.

6. An apparatus for measuring the turbidity of a liquid media, said apparatus comprising a cylindrical body, a light sensor including at least one optical fiber in said cylindrical body, said cylindrical body having a light-receiving surface and a measuring cell for holding the said liquid media to be analyzed, said cell having one closed end joined to said senor, another end which is open and upwardly directed, and means for intermittently cleaning the said light-receiving surface and for removing liquid media from said measuring cell.

7. The apparatus of claim 6, wherein the said means for cleaning the said light-receiving surface comprises a gas nozzle substantially facing the said light-receiving surface.

8. The apparatus of claim 7, wherein the said apparatus comprises a means for supplying, intermittently, gas under pressure to the said nozzle.

9. The apparatus of claim 8, wherein the said gas comprises air.

10. A method for the on-line measurement of microorganism concentration in a fermentation process, said method comprising:

(i) placing an apparatus for measuring the turbidity of the fermentation broth of said fermentation process in a fermentation broth, said apparatus comprising a cylindrical body, a light sensor including at least one optical fiber in said cylindrical body, said cylindrical body having a light-receiving surface and a measuring cell adjacent said light receiving surface for holding the said liquid media to be analyzed, wherein said light sensor comprises means for radiating light through said light-receiving surface and into said measuring cell, and further comprises means for detecting scattered light impinging on said light-receiving surface, said cell having one end joined to said sensor and other end which is open, and a means for intermittently cleaning the said light-receiving surface, wherein said apparatus is oriented in a direction permitting bubbles dissolved in the said fermentation broth within said measuring cell to float away therefrom and out of the cell through said open end and preventing bubbles outside of said cylindrical body from entering said cell;

(ii) introducing a portion of said fermentation broth into said measuring cell;

(iii) allowing bubbles in the said measuring cell to float out of the said cell;

(iv) radiating light in the said fermentation broth via the said optical fiber; and (v) detecting scattered light impinging on the said light-receiving surface.

11. A method of on-line measurement of the turbidity of a liquid media having gas bubbles therein, comprising the steps of:

isolating a portion of said liquid media in a measuring cell;

permitting bubbles in said isolated portion of said liquid media to float away from said isolated portion while preventing bubbles from a remainder of said liquid media from entering said isolated portion of said liquid media;

detecting radiated light scattered from said isolated portion of said liquid media via a light receiving surface; and removing staining matter from said light receiving surface and removing said isolated portion from said measuring cell by blowing a gas past said light receiving surface.

12. The method of claim 11, wherein said isolating and permitting steps together comprise placing in said liquid media a cylindrical body having an upwardly directed open end, said cylindrical body being otherwise closed, whereby bubbles can float out of said open end but cannot enter said open end.

13. The method of claim 12, wherein said cylindrical body has a light-receiving surface, including the step of intermittently blowing air past said light-receiving surface to clean said light-receiving surface.

14. An apparatus for on-line measurement of the turbidity of a liquid media having gas bubbles therein, comprising:

means for isolating a portion of said liquid media in a measuring cell;

means for permitting bubbles in said isolated portion of said liquid media to float away from said isolated portion while preventing bubbles from a remainder of said liquid media from entering said isolated portion;

means for radiating light into said isolated portion of said liquid media;

means for detecting radiated light scattered from said isolated portion of said liquid media via a light receiving surface; and means for removing staining matter from said light receiving surface and for removing said isolated portion from said measuring cell, said removing means comprising means for selectively blowing sufficient gas past said light receiving surface to remove staining matter therefrom and to remove said isolated portion from said measuring cell.

* * * * *